US009107692B2

(12) United States Patent
Boyden et al.

(10) Patent No.: US 9,107,692 B2
(45) Date of Patent: Aug. 18, 2015

(54) SWITCHABLE STERILIZING CUTTING SYSTEM

(75) Inventors: Edward S. Boyden, Palo Alto, CA (US); Roderick A. Hyde, Livermore, CA (US); Muriel Y. Ishikawa, Livermore, CA (US); Eric C. Leuthardt, St. Louis, MO (US); Nathan P. Myhrvold, Medina, WA (US); Dennis J. Rivet, St. Louis, MO (US); Michael A. Smith, San Gabriel, CA (US); Thomas A. Weaver, San Mateo, CA (US); Lowell L. Wood, Jr., Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1473 days.

(21) Appl. No.: 11/526,192

(22) Filed: Sep. 22, 2006

(65) Prior Publication Data

US 2008/0077123 A1    Mar. 27, 2008

Related U.S. Application Data

(63) Continuation-in-part of application No. 11/526,193, filed on Sep. 22, 2006, and a continuation-in-part of application No. 11/526,090, filed on Sep. 22, 2006.

(51) Int. Cl.
| | |
|---|---|
| *E04H 1/00* | (2006.01) |
| *A61B 17/3211* | (2006.01) |
| *A61B 17/3201* | (2006.01) |
| *A61B 19/00* | (2006.01) |
| *A61L 2/00* | (2006.01) |
| *A61L 2/10* | (2006.01) |
| *A61B 17/32* | (2006.01) |
| *A61B 17/00* | (2006.01) |

(52) U.S. Cl.
CPC .......... *A61B 17/3211* (2013.01); *A61B 17/3201* (2013.01); *A61B 19/38* (2013.01); *A61L 2/0011* (2013.01); *A61L 2/10* (2013.01); *A61B 17/32002* (2013.01); *A61B 2017/00022* (2013.01); *A61B 2017/00061* (2013.01); *A61B 2017/00084* (2013.01); *A61B 2019/464* (2013.01)

(58) Field of Classification Search
CPC .................... A61B 17/32002; A61B 17/3201; A61B 17/3211; A61B 19/38; A61L 2/0011; A61L 2/10
USPC ............................... 606/167, 10, 79
See application file for complete search history.

(56) References Cited

U.S. PATENT DOCUMENTS

| | | | | |
|---|---|---|---|---|
| 4,273,127 A | * | 6/1981 | Auth et al. ................. | 606/3 |
| 5,112,328 A | * | 5/1992 | Taboada et al. ............ | 606/4 |
| 5,260,020 A | * | 11/1993 | Wilk et al. ................. | 422/22 |
| 5,273,127 A | * | 12/1993 | Burg .......................... | 180/116 |
| 5,464,013 A | * | 11/1995 | Lemelson .................. | 600/427 |
| 5,571,098 A | | 11/1996 | Domankevitz et al. | |

(Continued)

OTHER PUBLICATIONS

Siddiqui, Salman; "Ultraviolet Radiation: Knowing All the Facts for Effective Water Treatment"; bearing a date of May 2004; pp. 11-13; located at www.wcponline.com/PDF/0504%20UV%20Radiation. pdf.

(Continued)

*Primary Examiner* — Thomas McEvoy
*Assistant Examiner* — Julie A Szpira

(57) ABSTRACT

Sectioning tools that emit self-sterilizing radiation. In one approach, the radiation is ultraviolet and/or plasmonic.

6 Claims, 5 Drawing Sheets

(56) References Cited

U.S. PATENT DOCUMENTS

| | | | |
|---|---|---|---|
| 5,772,597 A * | 6/1998 | Goldberger et al. | 600/473 |
| 5,951,543 A | 9/1999 | Brauer | |
| 6,056,741 A * | 5/2000 | Van Saarloos | 606/5 |
| 6,383,179 B1 | 5/2002 | Neuberger | |
| 6,421,128 B1 | 7/2002 | Salamon et al. | |
| 6,529,543 B1 * | 3/2003 | Anderson et al. | 372/108 |
| 6,551,346 B2 | 4/2003 | Crossley | |
| 6,744,790 B1 | 6/2004 | Tilleman et al. | |
| 7,054,528 B2 * | 5/2006 | Blumberg | 385/43 |
| 2002/0147443 A1 | 10/2002 | Ganz | |
| 2003/0007138 A1 | 1/2003 | Shigematsu et al. | |
| 2003/0018373 A1 | 1/2003 | Eckhardt et al. | |
| 2005/0203495 A1 * | 9/2005 | Malak | 606/9 |
| 2007/0213698 A1 * | 9/2007 | Altshuler et al. | 606/12 |
| 2007/0239146 A1 | 10/2007 | Wang | |

OTHER PUBLICATIONS

"Sure Blade™ Diamond LaserKnife"; Clinicon.com; printed on Sep. 19, 2006; pp. 1-3; located at http://www.clinicon.com/diamondlaser.html.

PCT International Search Report; International App. No. PCT/US07/20417; Aug. 1, 2008; pp. 1-2.

* cited by examiner

SWITCHABLE STERILIZING CUTTING SYSTEM

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

1. For purposes of the USPTO extra-statutory requirements, the present application constitutes a continuation-in-part of U.S. patent application Ser. No. 11/526,193, entitled STERILIZING CUTTING SYSTEM, naming Edward S. Boyden, Roderick A. Hyde, Muriel Y. Ishikawa, Eric C. Leuthardt, Nathan P. Myhrvold, Dennis J. Rivet, Michael A. Smith, Thomas A. Weaver, and Lowell L. Wood, Jr. as inventors, filed 22 Sep. 2006, which is currently co-pending, or is an application of which a currently co-pending application is entitled to the benefit of the filing date.

2. For purposes of the USPTO extra-statutory requirements, the present application constitutes a continuation-in-part of U.S. patent application Ser. No. 11/526,090, entitled STERILIZING CUTTING METHOD, naming Edward S. Boyden, Roderick A. Hyde, Muriel Y. Ishikawa, Eric C. Leuthardt, Nathan P. Myhrvold, Dennis J. Rivet, Michael A. Smith, Thomas A. Weaver, and Lowell L. Wood, Jr. as inventors, filed 22 Sep. 2006, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present applicant entity has provided above a specific reference to the application(s) from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, applicant entity understands that the USPTO's computer programs have certain data entry requirements, and hence applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

In one aspect, an apparatus for sectioning a material includes a first member including a sectioning structure (e.g., a cutting edge or a cauterizer such as an electrocauterizer) and an optical guiding structure. The optical guiding structure has a first portion coupled to the cutting edge and a second portion separated from the first portion, wherein the guiding structure is configured to propagate ultraviolet energy from the second portion to the first portion. The guiding structure may be integral to the first member. The first member may include at least one output coupling structure (e.g., an internally reflective surface) configured to direct ultraviolet energy from the guiding structure towards the sectioning structure. The apparatus may include an energy blocking structure (e.g., an opaque and/or ultraviolet opaque coating such as a metal coating) which may be positioned between the sectioning structure and an expected grip region and/or between the sectioning structure and an expected viewing location. The apparatus may include a region shaped for grasping, which may include an energy blocking structure such as an opaque and/or ultraviolet opaque coating (e.g., a metal coating). The apparatus may further include a converting structure configured to convert ultraviolet energy to plasmon energy, which may include a metal coating such as a silver coating, and the optical guiding structure may include a plasmon guiding structure. At least a portion of the first member may be at least partially transparent to ultraviolet energy, and the first member may include diamond and/or quartz. The optical guiding structure may include a waveguide and/or an optical fiber, and may be configured to propagate the ultraviolet energy to substantially all of the sectioning structure. The sectioning structure may include, for example, a cutting edge, a piercing structure, and/or a cauterizer such as an electrocauterizer.

In another aspect, an apparatus for sectioning a material includes a first member including a sectioning structure and an ultraviolet emitter (e.g., a laser) optically coupled to the sectioning structure. The apparatus may further include an optical guiding structure having a first portion coupled to the sectioning structure and a second portion coupled to the ultraviolet emitted, the guiding portion being configured to propagate ultraviolet energy from the second portion to the first portion. The guiding structure may be integral to the first member, and may include a waveguide and/or an optical fiber. The first member may include at least one output coupling structure (e.g., an internally reflective surface) configured to direct ultraviolet energy from the guiding structure towards the sectioning structure. The apparatus may include an ultraviolet blocking structure (e.g., an opaque and/or ultraviolet opaque coating such as a metal coating) between the sectioning structure and an expected grip location and/or between the sectioning structure and an expected viewing location. The apparatus may include a handle, which may include an ultraviolet blocking structure such as an opaque and/or ultraviolet opaque coating (e.g., a metal coating). The apparatus may include a converter configured to convert ultraviolet emissions to plasmon emissions, such as a metal (e.g., silver) layer. The ultraviolet emitter may be configured to direct ultraviolet energy through the sectioning structure, and may be positioned on a surface of the first member and/or on the sectioning structure. The ultraviolet emitted may be configured to emit radiation having a wavelength of less than about 300 nm (e.g., radiation having a wavelength between about 230 nm and about 280 nm). The sectioning structure may include a cutting edge, a piercing structure, and/or a cauterizer such as an electrocauterizer.

In yet another aspect, an apparatus includes a first member including a sectioning structure, an ultraviolet emitter (e.g., a laser) optically coupled to the sectioning structure, and a switch configured to modulate the ultraviolet emitter in response to a signal condition. The switch may be configured for manual activation, or it may modulate the ultraviolet emitter when the sectioning structure is in contact with a material. The apparatus may include a proximity sensor (e.g., a capacitive sensor, an optical sensor, and/or a receiver responsive to a carrier signal in the material) that determines proximity of the sectioning structure to a material, in which case the switch may be configured to modulate the ultraviolet emitter in response to the proximity sensor. The switch may be configured to modulate the ultraviolet emitter in response to a temperature sensor, to a reflectivity sensor that is configured to detect reflectivity in the vicinity of the sectioning structure, to a biological sensor that is configured to detect a presence of microorganisms in the vicinity of the sectioning structure, and/or to a force sensor. Modulating the ultraviolet emitter may include activating or deactivating the ultraviolet emitter. The ultraviolet emitter may be configured to emit radiation having a wavelength of less than about 300 nm (e.g., radiation having a wavelength between about 230 nm and about 280 nm).

In still another aspect, a method of sectioning includes contacting a material with a sectioning surface of a sectioning tool (e.g., a knife, scissor, rotary cutter, and/or a cauterizer), and emitting sterilizing radiation from the sectioning surface of the sectioning tool. Contacting the material with the sectioning surface of the sectioning tool may include cutting, cauterizing, dissecting, and/or piercing the material. Emission of the sterilizing radiation may be substantially concurrent or alternate with contacting the material with the sectioning surface. The material may be biological tissue, which may be human, animal, or plant tissue and may be alive or nonliving. The tissue may be an organ (e.g., a cardiovascular organ, a digestive organ, an endocrine system organ, an immune system organ, an integumentary system organ, a lymphatic organ, a musculoskeletal organ, a nervous system organ, a reproductive organ, a respiratory organ, and/or a urinary organ). The sectioning surface may be at least partially transparent to the sterilizing radiation (e.g., diamond or quartz). The radiation may be ultraviolet radiation, which may have a wavelength of less than about 300 nm (e.g., radiation having a wavelength between about 230 nm and about 280 nm).

In a further aspect, a method of sectioning includes contacting a material with a sectioning surface of a sectioning tool (e.g., a knife, scissor, rotary cutter, and/or a cauterizer), and directing sterilizing radiation from an integrated emitter onto the sectioning surface of the sectioning tool. Contacting the material with the sectioning surface of the sectioning tool may include cutting, cauterizing, dissecting, and/or piercing the material. Emission of the sterilizing radiation may be substantially concurrent or alternate with contacting the material with the sectioning surface. The material may be biological tissue, which may be human, animal, or plant tissue and may be alive or nonliving. The tissue may be an organ (e.g., a cardiovascular organ, a digestive organ, an endocrine system organ, an immune system organ, an integumentary system organ, a lymphatic organ, a musculoskeletal organ, a nervous system organ, a reproductive organ, a respiratory organ, and/or a urinary organ). The radiation may be ultraviolet radiation, which may have a wavelength of less than about 300 nm (e.g., radiation having a wavelength between about 230 nm and about 280 nm).

In yet a further aspect, a control system for a sectioning tool includes a sensor that senses a condition in the vicinity of the sectioning tool, and a sensor logic that generates a signal in response to the sensor, wherein the generated signal is configured to modulate sterilizing radiation at a sectioning surface of the sectioning tool. The sensor may include a proximity sensor (e.g., a capacitive sensor, an optical sensor, and/or an antenna), a reflectivity sensor, a biological sensor, and/or a force sensor. The generated signal may be configured to increase or decrease the amplitude of the sterilizing radiation, or to initiate or terminate the sterilizing radiation. The sensor logic may include electrical circuitry.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
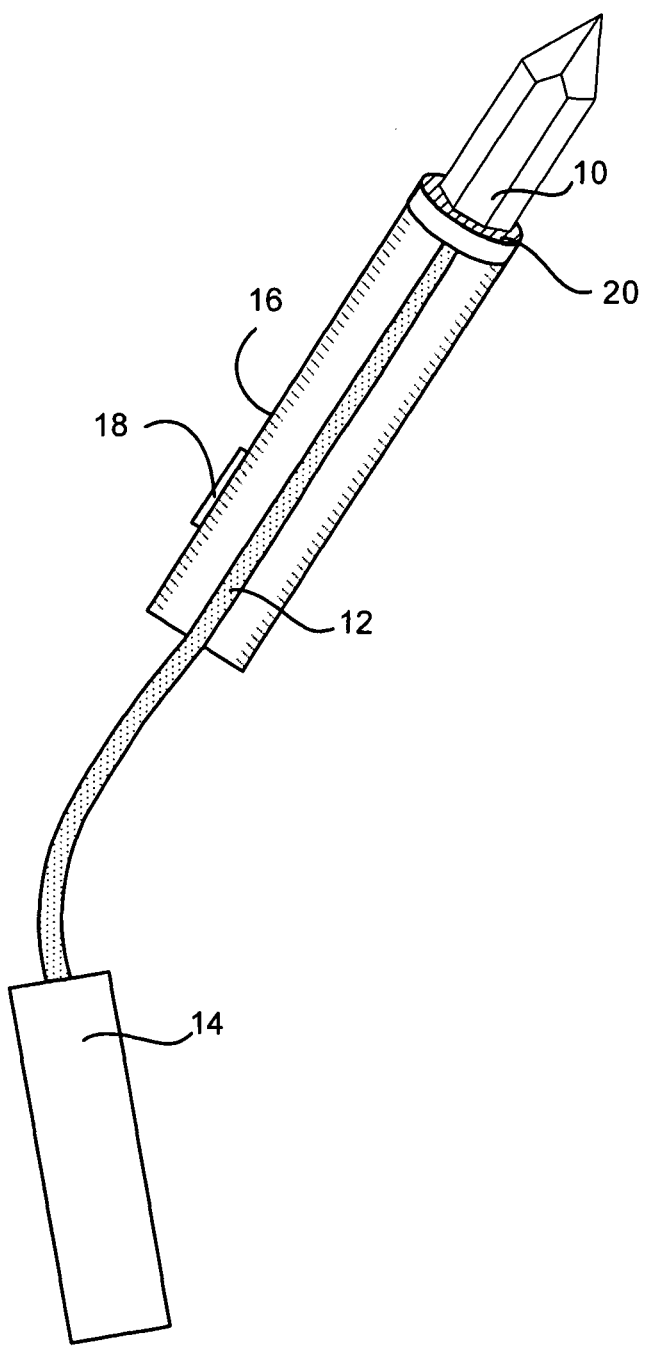
FIG. 1 is a schematic representation of a cutting instrument.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Iatrogenic infections are believed to be increasing in seriousness, due in part to the development of antibiotic-resistant bacteria. While postoperative infection is a relatively rare occurrence for modern surgeons, infections of surgical sites do occur and may require extensive follow-up treatment. It is currently believed that many such infections are due to the entry of normal skin flora into the surgical site, which may occur due to transport on scalpels and other sectioning tools (e.g., cauters, trocars, needles, drills, curettes, and/or staples). The sectioning tools described herein may mitigate such infections by sterilizing some or all of the portions of the tools contacting the patient and their surroundings, either intermittently or continuously, before, during, and/or after surgery.

FIG. 1 shows a surgical instrument, suitable for a variety of surgeries including ophthalmologic surgery. The instrument includes a cutting blade 10, which is at least partially transparent to sterilizing radiation (for example, ultraviolet (UV) radiation having a wavelength of less than about 300 nm, or blue light). In other embodiments, the instrument may include a piercing structure (such as a syringe). In some embodiments, the cutting blade 10 may be partially or completely made of quartz or of diamond, or may be coated with such materials. The instrument shown also includes a guiding structure 12, which may be an optical fiber, a waveguide, or any other structure suitable for transmitting sterilizing radiation, and a sterilizing radiation source 14 (e.g., a UV laser or a mercury vapor lamp). In other embodiments, sterilizing radiation source 14 may be directly connected to cutting blade 10 without need for guiding structure 12. As shown, the instrument further includes a handle 16 and a manual switch 18. The manual switch 18 may be configured to modulate the emission of radiation of source 14, for example by turning the source on or off, by increasing or decreasing the intensity of radiation from the source, by changing the wavelength of the source, and/or by changing the strobe frequency and/or strobe duration of a stroboscopic source. In addition or in the alternative, the manual switch 18 may modulate the transmission of sterilizing radiation through the guiding structure 12. Other embodiments may include other circuitry for modulating the delivery of radiation as discussed further below. While manual switch 18 is positioned on the scalpel, the switch may also be, for example, a foot switch, a head-mounted switch, a voice-activated switch, and/or a remote switch.

Figure 2:
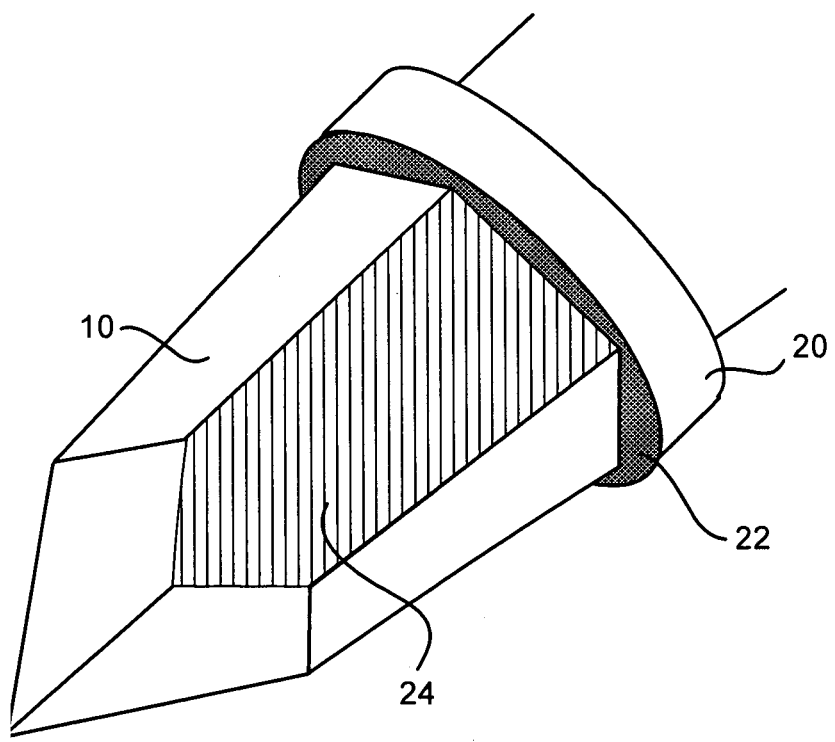
FIG. 2 is a schematic representation of a cutting blade.

FIG. 2 shows the tip of the instrument of FIG. 1. As shown, cutting blade 10 is secured in a collar 20. A sensor 22 is positioned on the front face of the collar 20. Sensor 22 may be, for example, a proximity sensor, a temperature sensor, a biological sensor, and/or a reflectivity sensor. Radiation source 14 and/or guiding structure 12 may be adjusted to modulate sterilizing radiation reaching cutting blade 10 in response to a signal from sensor 22.

While the illustrative embodiment of FIG. 1 shows a manual switch, some embodiments may control and/or activate the sterilizing radiation automatically or semi-automatically in response to input signals, timers or other appropriate structures. Such signals, timers, or other structures may be implemented through electrical circuitry, mechanical approaches, or a variety of other approaches to controlling duration, amount, intensity, focus or other parameters of sterilizing radiation.

In one illustrative approach, a switch may reduce radiation levels responsive to an external sensor such as a temperature sensor that indicates that the instrument is close to warm living tissue. Such an approach can reduce exposure of tissue to potentially harmful ultraviolet radiation. Alternatively, the switch may increase radiation levels near living tissue, thereby selectively increasing exposure to radiation, which may enhance sterilization. The switch may similarly increase or decrease radiation levels when a proximity sensor (e.g., a capacitive sensor, an optical sensor, or an antenna that senses a carrier signal in the material to be cut) indicates that the cutting instrument is near the material to be cut. The switch may increase radiation levels when a biological sensor indicates that particular microorganisms are detected, or may reduce radiation levels to avoid reflecting sterilizing radiation into a user's eyes when a reflectivity sensor indicates that the instrument is approaching a high-reflectivity surface. The switch may adjust levels in response to a self-motion sensor (e.g., an inertial sensor or an external tracking system that monitors instrument position), for example to increase intensity during rapid movement of the instrument, which may tend to equalize the dose of radiation delivered to any region of tissue. In addition to modulating radiation intensity, the switch may modulate other characteristics of the sterilizing radiation such as frequency and phase, manually and/or in response to one or more sensors.

In some embodiments, energy may be transmitted through the guiding structure 12 and converted to sterilizing radiation at the cutting blade 10. In one such embodiment, optical radiation may be transmitted through the guiding structure and converted to plasmon radiation by a conversion structure, such as a thin silver layer 24 located on part or all of the cutting blade 10. While the illustrative conversion structure is presented as the thin silver layer 24, other conversion structures can produce plasmonic radiation proximate the cutting blade 10. For example, the cutting blade 10 may include a layered dielectric that prevents radiation other than evanescent waves from escaping the cutting blade 10. Since evanescent waves are typically extremely localized in nature, the sterilizing radiation in such embodiments may be confined to the surface of the cutting blade 10, potentially avoiding exposure of other tissue.

In one embodiment, sterilizing radiation such as ultraviolet radiation is directed into the cutting blade 10 at a sufficiently shallow angle to the surface that it is totally internally reflected when the blade 10 is exposed to air, but is transmitted outward when the cutting blade 10 is in contact with a higher-index material (e.g., water, or the body of a cell). In this embodiment, the sterilizing radiation may efficiently be directed only or primarily into cells on the surface of the cutting blade 10. Alternately, the radiation may be totally internally reflected along the body of the blade, and able to escape only at the faceted tip.

In other embodiments, the cutting blade 10 may include a variety of modulating structures that shift phase, frequency, intensity, or other characteristics of radiation, such as but not limited to lenses, mirrors, gratings, polarizers, or filters. Any of these modulating structures may be either active or passive.

Handle 16 may include a blocking structure that blocks sterilizing radiation from reaching certain areas. For example, the handle may prevent radiation from reaching the surgeon's hand and/or eyes. The blocking structure may comprise a layer of metal or other radiation-blocking material. The structure may also have a reflecting or focusing effect, guiding the radiation towards the cutting blade 10.

The frequency and intensity of radiation may be selected to achieve the degree of sterilization required. In general, ultraviolet radiation in the range of about 230 to about 280 nm (UV-C) is considered to have a strong germicidal effect, with dosages of about 1-50 mJ/cm$^2$ being sufficient to inhibit colony formation and/or to kill most bacteria and viruses (see Siddiqui, "Ultraviolet Radiation: Knowing All the Facts for Effective Water Treatment," *Water Conditioning & Purification*, May 2004:11-13, which is incorporated by reference herein).

Figure 3:
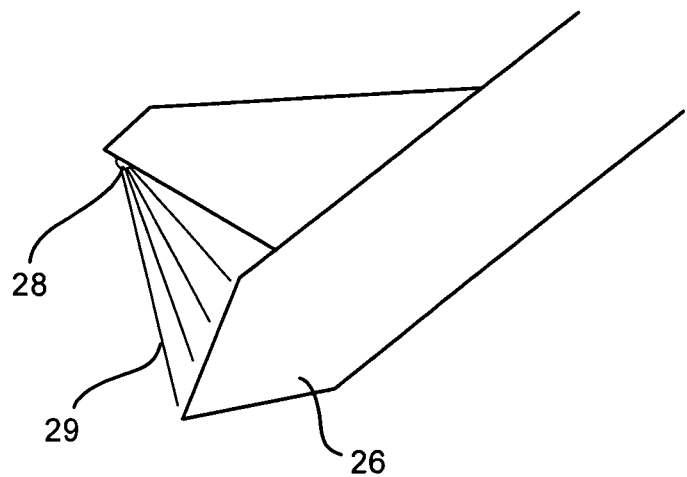
FIG. 3 is a schematic representation of another cutting instrument.

FIG. 3 shows another cutting device suitable for use in surgery. The device includes a cutting blade 26, and an integrated radiation source 28 that directs sterilizing radiation 29 towards the cutting blade 26. Sterilizing radiation may be generated at the radiation source 28, or it may be guided by an optical guiding structure (not shown) to the output location shown where it is directed onto the cutting blade. As with the embodiment illustrated in FIGS. 1 and 2, radiation may be controlled by a manual switch and/or by a fully or semi-automatic switch responsive to one or more input signals, timers, or other appropriate control devices. The cutting blade 26 may, but need not, propagate the sterilizing radiation.

Figure 4:
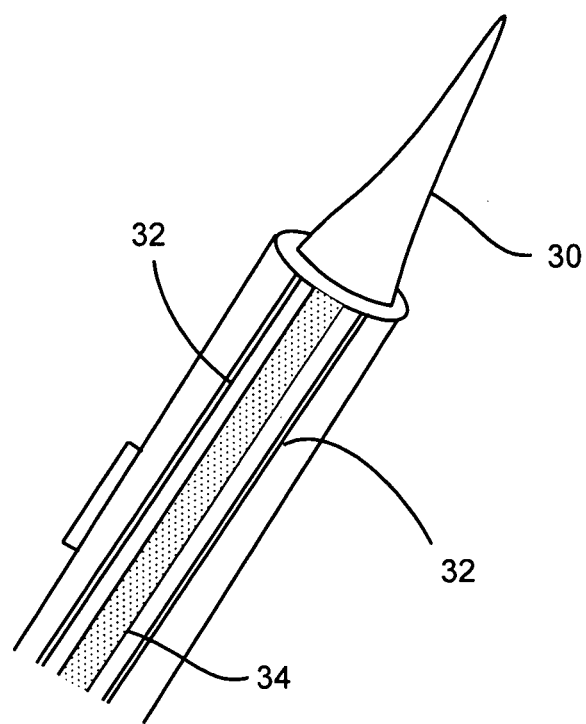
FIG. 4 is a schematic representation of an electrocauterizer.

FIG. 4 shows an electrocautery device. Cauterizing tip 30 is connected via leads 32 to an electrical supply (not shown). Cauterizing tip 30 is also connected to a guiding structure 34 suitable for transmitting sterilizing radiation from a radiation source (not shown). In other embodiments, a radiation source may be directly coupled to cauterizing tip 30 without need for guiding structure 34. In some embodiments, the sterilizing radiation may be ultraviolet radiation. In these or other embodiments, the radiation may be converted into a sterilizing form by a converting structure at the cauterizing tip 30, such as a thin silver layer that converts a conventional wave to an evanescent (plasmon) form.

The sectioning tools described above may be used for surgery on humans and/or animals, including surgery on cardiovascular organs (e.g., the heart, veins, and/or arteries), digestive organs (e.g., the mouth, pharynx, esophagus, stomach, small intestine, large intestine, liver, gall bladder, and/or pancreas), endocrine system organs (e.g., the hypothalamus, pineal gland, pituitary gland, thyroid gland, parathyroid gland, adrenal gland, and/or kidney), immune system organs (e.g., the bone marrow, thymus gland, adenoids, tonsils, spleen, lymph nodes, lymph ducts, lymph vessels, and/or the appendix), skin, nervous system organs (e.g., the brain, spine, and/or nerves), reproductive organs (e.g., the penis, prepuce, testicles, scrotum, prostate, seminal vesicles, epididymis, Cowper's glands, vulva, vagina, cervix, uterus, placenta, Fallopian tubes, ovaries, Skene's glands, and/or Bartholin's glands), respiratory organs (e.g., the nose, mouth, trachea, bronchi, lungs, and/or diaphragm), musculoskeletal system (e.g., the muscles, bones, cartilage, ligaments, and/or tendons), and urinary organs (e.g., the kidney, ureter, and/or bladder). "Sectioning" may include any means of physically dividing a material, including without limitation cutting, dissecting, incising, piercing, cleaving, drilling, curetting, or perforating. Materials to be sectioned include without limitation anything in or to be placed in the body, whether natural or implanted, including organs, sutures, grafts, catheters, wires, implant devices (e.g., metal, ceramic, and/or plastic implants), and/or transplanted tissue (e.g., allograft, autograft, and/or xenograft), and further include food items such as meat, vegetable, and/or dairy products.

In some embodiments, the sectioning tools and methods described above may be well-adapted for invasive procedures when these procedures must be performed in relatively non-sterile environments, such as emergency procedures at a trauma scene, in an ambulance, on a battlefield, or at a campsite. They may be appropriate for outpatient procedures at a doctor's office where conditions are typically less sterile than in an operating room, or for veterinary procedures that must sometimes be performed under extremely nonsterile conditions (e.g., routine castration of meat animals).

Figure 5:
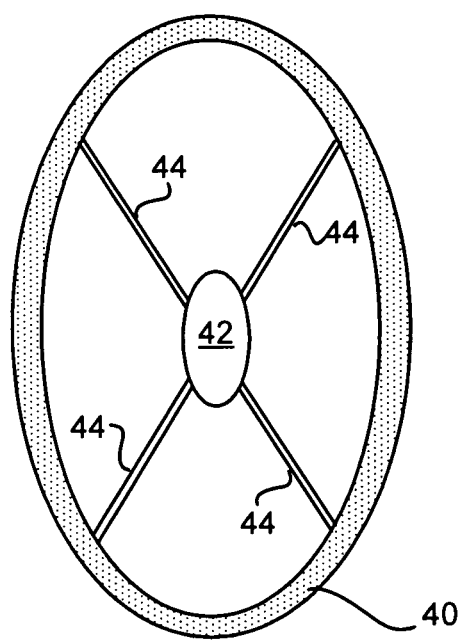
FIG. 5 is a schematic representation of a rotary cutter.

The sterilization of cutting and sectioning tools is of increasing concern in the slaughterhouse and meat packing industries, in part but not entirely due to the rise in incidence of bovine spongiform encephalopathy (BSE). FIG. 5 shows a sawing device for use in butchery. Self-sterilizing radiation may be used with a variety of slaughterhouse and meat packing equipment, including without limitation cutters, handlers, trimmers, grinders, rendering equipment, and/or mechanical meat separators; the instrument shown in FIG. 5 is a rotary cutter. Cutting surface 40 includes a material selected to be partially or fully transparent to sterilizing radiation (e.g., to ultraviolet radiation). Radiation is delivered from radiation source 42 to cutting surface 40 via one or more guiding structures 44, which in FIG. 4 are arranged as spokes in a wheel. Cutting surface 40 may further be constructed to guide radiation along the circumference in order to reach more of the cutting surface.

In use, the sawing device of FIG. 5 may emit sterilizing radiation continuously during meat cutting, or the sterilizing radiation may be switched on and off. For example, in some embodiments, it may be desirable not to "cook" the surface of the meat during cutting, but the sterilizing radiation may be switched on to sterilize the cutter between cuts, potentially minimizing cross-contamination of the cutter from one carcass to the next. In some such embodiments, the cutter may include a sensor that automatically deactivates (or otherwise modulates) the radiation when the cutter is in contact with the meat. The sensor may be, for example, a proximity sensor (e.g., a capacitive or optical sensor), a temperature sensor, an antenna that senses a carrier signal in the meat, or a force sensor that senses load on the rotary cutter or weight of a carcass being brought into position for cutting. In other embodiments, the sterilizing radiation may be activated when in contact with the meat by use of a similar sensor.

The sterilizing methods and self-sterilizing tools described above may also be used for the preparation of other foods, and for other agricultural and veterinary uses. For example, automated harvesting equipment may self-sterilize by emission of radiation, thereby reducing spread of blight and other plant infections in a field. Self-sterilizing food preparation and packaging equipment may reduce food-borne infections (e.g., bacterial infections in bagged salads) by reducing contamination of foodstuffs. Knives, needles, and other sectioning instruments that are typically carried by outdoorsmen and/or soldiers may be field-sterilized to reduce chances of infection, for example when they are used for food preparation (e.g., cleaning fish and game) or for invasive procedures ranging from minor (e.g., splinter removal) to major (e.g., emergency tracheotomy).

While the illustrative implementations described herein include a variety of structures that provide sterilizing radiation near a cutting edge or similar area, such approaches may be combined with other forms of sterilization, such as a broader area ultraviolet radiation or x-ray radiation, as appropriate.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus, comprising:
   a first member including a sectioning structure;
   a radiation emitter optically directed to the sectioning structure;
   a conversion structure positioned at the sectioning structure and configured to convert radiation from the radiation emitter to sterilizing radiation; and
   a switch configured to modulate the radiation emitter by reducing a radiation level in response to proximity to a material, wherein the switch is further configured to modulate the radiation emitter in response to a force sensor.

2. An apparatus, comprising:
   a first member including a sectioning structure;
   a radiation emitter optically directed to the sectioning structure;

a conversion structure positioned at the sectioning structure and configured to convert radiation from the radiation emitter to sterilizing radiation; and a switch configured to modulate the radiation emitter by reducing a radiation level in response to proximity to a material, wherein the switch is further configured to modulate the radiation emitter in response to a motion sensor.

3. An apparatus, comprising:

a first member including a sectioning structure;

a radiation emitter optically directed to the sectioning structure;

a conversion structure positioned at the sectioning structure and configured to convert radiation from the radiation emitter to sterilizing radiation; and a switch configured to modulate the radiation emitter by reducing a radiation level in response to proximity to a material, wherein modulating the radiation emitter includes deactivating the radiation emitter.

4. A control system for a sectioning tool, comprising:

a sensor that senses a condition in the vicinity of the sectioning tool indicative of proximity to a material, and a sensor logic that generates a signal in response to the sensor, wherein the generated signal is configured to reduce sterilizing radiation produced at a sectioning surface of the sectioning tool, wherein the sensor comprises a force sensor.

5. A control system for a sectioning tool, comprising:

a sensor that senses a condition in the vicinity of the sectioning tool indicative of proximity to a material, and a sensor logic that generates a signal in response to the sensor, wherein the generated signal is configured to reduce sterilizing radiation produced at a sectioning surface of the sectioning tool, wherein the sensor comprises a motion sensor.

6. A control system for a sectioning tool, comprising:

a sensor that senses a condition in the vicinity of the sectioning tool indicative of proximity to a material, and a sensor logic that generates a signal in response to the sensor, wherein the generated signal is configured to reduce sterilizing radiation produced at a sectioning surface of the sectioning tool, wherein the generated signal is configured to terminate the sterilizing radiation.

* * * * *